(12) United States Patent
Johnson

(10) Patent No.: US 7,161,665 B2
(45) Date of Patent: Jan. 9, 2007

(54) HIGH RESOLUTION IMAGING FOUNTAIN FLOW CYTOMETRY

(75) Inventor: Paul E. Johnson, Laramie, WY (US)

(73) Assignee: University of Wyoming, Laramie, WY (US)

( * ) Notice: Subject to any disclaimer, the term of this patent is extended or adjusted under 35 U.S.C. 154(b) by 394 days.

(21) Appl. No.: 10/849,477

(22) Filed: May 19, 2004

(65) Prior Publication Data

US 2005/0036139 A1 Feb. 17, 2005

Related U.S. Application Data

(63) Continuation-in-part of application No. 10/323,535, filed on Dec. 18, 2002, now Pat. No. 6,765,656.

(51) Int. Cl.
*G01N 21/00* (2006.01)

(52) U.S. Cl. .......................................... 356/73; 356/338

(58) Field of Classification Search ...................... None
See application file for complete search history.

(56) References Cited

U.S. PATENT DOCUMENTS 4,756,427 A * 7/1988 Gohde et al. ................ 209/3.1
5,488,469 A * 1/1996 Yamamoto et al. ............ 356/72
6,154,276 A * 11/2000 Mariella, Jr. ................. 356/337
6,188,474 B1 * 2/2001 Dussault et al. ............ 356/246
6,309,886 B1 * 10/2001 Ambrose et al. ............. 436/63

FOREIGN PATENT DOCUMENTS

EP 0333560 * 9/1989

* cited by examiner

*Primary Examiner*—Michael P. Stafira
(74) *Attorney, Agent, or Firm*—Macheledt Bales & Heidmiller, LLP; Jennifer L. Bales (57) ABSTRACT

An imaging fountain flow cytometer allows high resolution microscopic imaging of a flowing sample in real time. Cells of interest are in a vertical stream of liquid flowing toward one or more illuminating elements at wavelengths which illuminate fluorescent dyes and cause the cells to fluoresce. A detector detects the fluorescence emission each time a marked cell passes through the focal plane of the detector. A bi-directional syringe pump allows the user to reverse the flow and locate the detected cell in the field of view. The flow cell is mounted on a computer controlled x-y stage, so the user can center a portion of the image on which to zoom or increase magnification. Several computer selectable parfocal objective lenses allow the user to image the entire field of view and then zoom in on the detected cell at substantially higher resolution. The magnified cell is then imaged at the various wavelengths.

26 Claims, 9 Drawing Sheets

PANEL A: SCHEMATIC OF A PROKARYOTIC CELL, SHOWING INDICATING THE NUCLEUS AND MITOCHONDRIA

FIG. 5B

PANEL B: IMAGE OF THE CELL TAKEN THROUGH A BLUE FILTER AFTER THE CELL HAS BEEN LABELED WITH A BLUE FLUORESCENT DYE ABSORBED BY DNA IN THE NUCLEUS AND A RED FLUORESCENT DYE ABSORBED BY THE MITOCHONDRIA

FIG. 5C

PANEL C: IMAGE OF THE SAME CELL TAKEN THROUGH A RED FILTER

FIG. 5D

PANEL D: IMAGE FORMED BY FALSE COLORING AND ADDING THE IMAGES FROM B AND C.

HIGH RESOLUTION IMAGING FOUNTAIN FLOW CYTOMETRY

This application is a Continuation in Part of U.S. patent application Ser. No. 10/323,535, filed Dec. 18, 2002 now U.S. Pat. No. 6,765,656, and incorporates that application by reference.

BACKGROUND OF THE INVENTION

1. Field of the Invention

The present invention relates to apparatus and methods for high resolution imaging and classification of sample particles in translucent or transparent flowing liquid. In particular, the present invention relates to high throughput analysis of imaged particles in a translucent flow.

2. Description of the Prior Art

Imaging and classification of low concentrations of selected target particles, cells in particular, in large volumes of fluid has a number of applications including: 1) bioterrorism and biowarfare defense, 2) food and water quality control, 3) clinical detection of cancerous cells, and 4) environmental monitoring. Cell imaging and classification systems developed to date usually suffer from 1) high cost, 2) unsatisfactory sensitivity, 3) slowness, 4) large size, 5) insufficient spectral and/or spatial resolution, and/or 6) labor-intensive preparation steps.

Direct detection may be accomplished using flow cytometry. Flow cytometry is a commonly used technique to measure the chemical or physical properties of cells. Cells flow by a measuring apparatus in single file while suspended in a fluid, usually air or water. In immunofluorescence flow cytometry, cells can be identified by attaching fluorescent antibodies to each cell:

An antibody specific to the cell of interest is labeled with a fluorescent molecule or fluorochrome.

The labeled antibody is mixed in solution with the cell of interest. The antibodies attach to specific sites on the cells (called antigens).

The cells are passed in single file in a stream of liquid past a laser(s), which illuminates the fluorochromes and causes them to fluoresce at a different wavelength.

A photomultiplier or photodiode is used to detect a burst of fluorescence emission each time a marked cell passes in front of the detector.

The number of marked cells can then be counted. Antibodies can be chosen that are highly-specific to the cell(s) of interest.

Flow cytometry is currently used for a wide variety of applications including: measuring helper T-lymphocyte counts to monitor HIV treatment, measuring tumor cell DNA content in determining cancer treatment, and separating X- and Y-chromosome bearing sperm for animal breeding.

Figure 1:
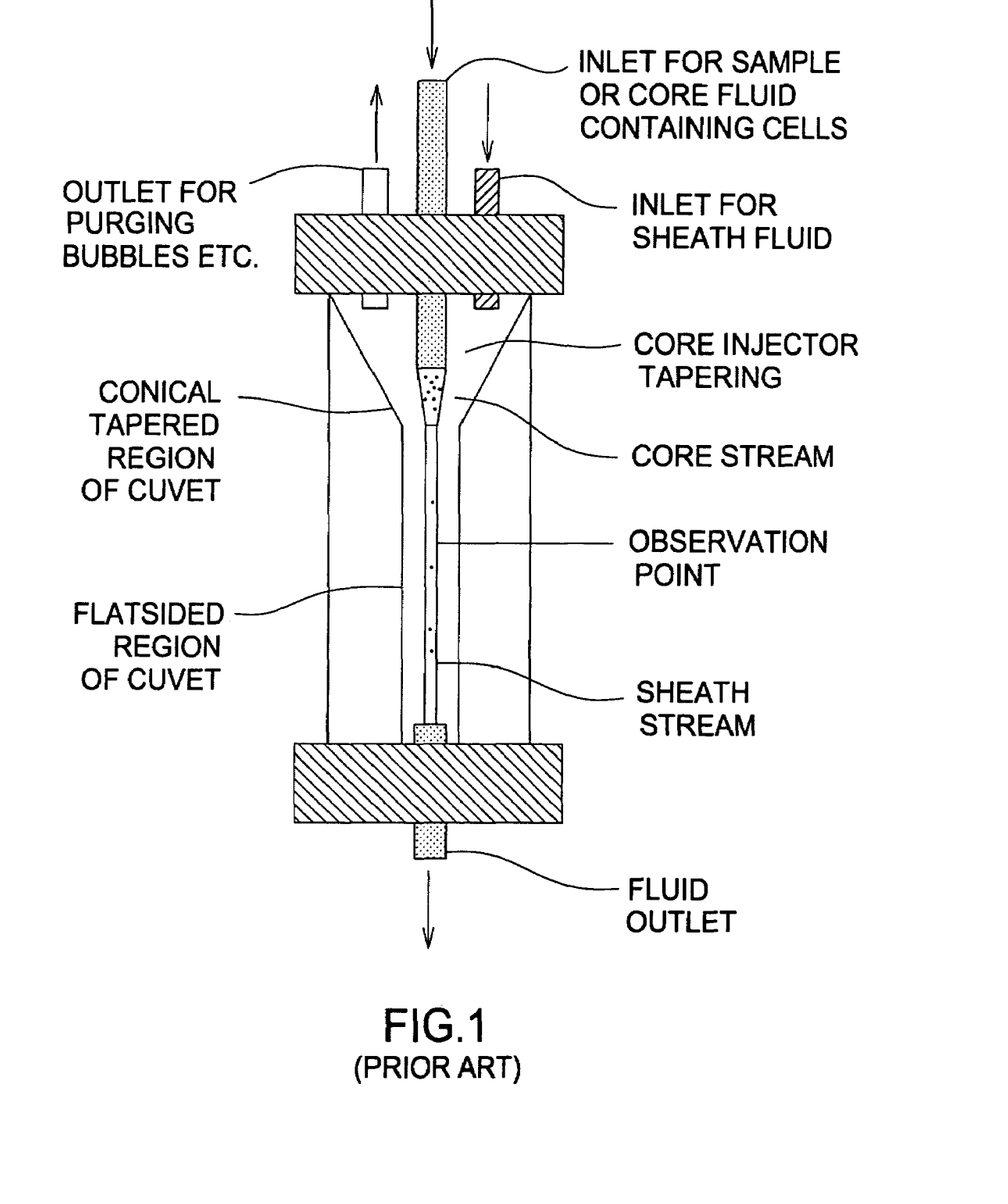
FIG. 1 (Prior Art) is a schematic drawing showing a conventional flow cytometry system.

FIG. 1 (prior art) shows a typical flow cytometry system (from Shapiro, Practical Flow Cytometry, 2nd Edition). Putting flow cytometry into practice involves using two concentric cylindrical streams of fluid. The inner flow or core flow contains the cells to be sampled. The purpose of the outer stream or sheath flow is to reduce the diameter of the core flow. As the core and sheath fluids reach the tapered region of the flow, the cross-sectional area of the core flow is reduced. A small bore core flow (about 20 microns) allows for precision photometric measurements of cells in the flow, illuminated by a small diameter laser beam; all of the cells will pass through nearly the same part of the beam and will be equally illuminated. Why not just pass the cells through a small-bore transparent tube? Small diameter orifices are generally unworkable because they experience frequent clogging. All commercial flow cytometers now use a sheath/core flow arrangement.

Laser-induced fluorescence of fluorescent labels in a flow cytometer is a uniquely powerful method of making fast, reliable, and relatively unambiguous detections of specific microorganisms, such as food-borne pathogens. Several monographs describe the methods and applications of flow cytometry (e.g., Flow Cytometry: First Principles by A. L. Givan, 1992, and references therein).

Historically, flow cytometers have been very large, expensive, laboratory-based instruments. They consume large amounts of power, and use complex electronics. They are not typically considered within the realm of portable devices. The size (desktop at the smallest), power requirements, and susceptibility to clogging (requiring operator intervention) of conventional flow cytometers precludes their use for many applications, such as field monitoring of water biocontamination.

U.S. Pat. No. 6,309,886, "High throughput analysis of samples in flowing liquid," by Ambrose et al. discloses an invention for the high throughput analysis of fluorescently labeled DNA in a transparent medium. This invention is a device that detects cells in a flow moving toward an imaging device. The flow is in a transparent tube illuminated in the focal plane from the side by a laser with a highly elongated beam. Although this invention does not suffer from the drawbacks listed above for alternative technologies, it is not suitable for applications where the flow medium is not transparent. It is also not an imaging technology, but rather a technology suitable for single-point photometric detection and characterization.

U.S. Pat. No. 6,473,176 (Baseji et al.), U.S. Pat. No. 6,249,341 (Baseji et al.), and U.S. Pat. No. 6,211,955 (Baseji et al.) describe a method to perform multi-spectral imaging of cells in a sample flowing in a flow cytometer using a technique called Time Delayed Integration or TDI. TDI is used with charge coupled device (CCD) detectors to produced enhanced signal-to-noise images of a moving scene (such as cells in a flow). The pixels of the CCD are arranged in rows and columns, and the signal is moved from row to row in synchrony with a moving image projected onto the device, allowing an extended integration time without blurring. Time Delayed Integration Multi-spectral flow cytometry, as described in the three above-mentioned patents, has advantages over previous flow cytometric techniques in that it recovers not only the fluorescence and/or scattering parameters from cells in the flow, but provides multi-spectral imaging as well. The latter allows for cell classification and differentiation based characteristics such as cell shape, overall size, nuclear size, nuclear shape, optical density, the detection and characterization of numerous fluorescent markers and FISH probes, the quantification of the total amount of DNA in the nucleus, and the detection of other cellular components at multiple wavelengths. The main disadvantage of this technique is that it requires TDI as well as conventional flow cytometry with all of its complexities including a hydrodynamically focused sheath flow.

Figure 2:
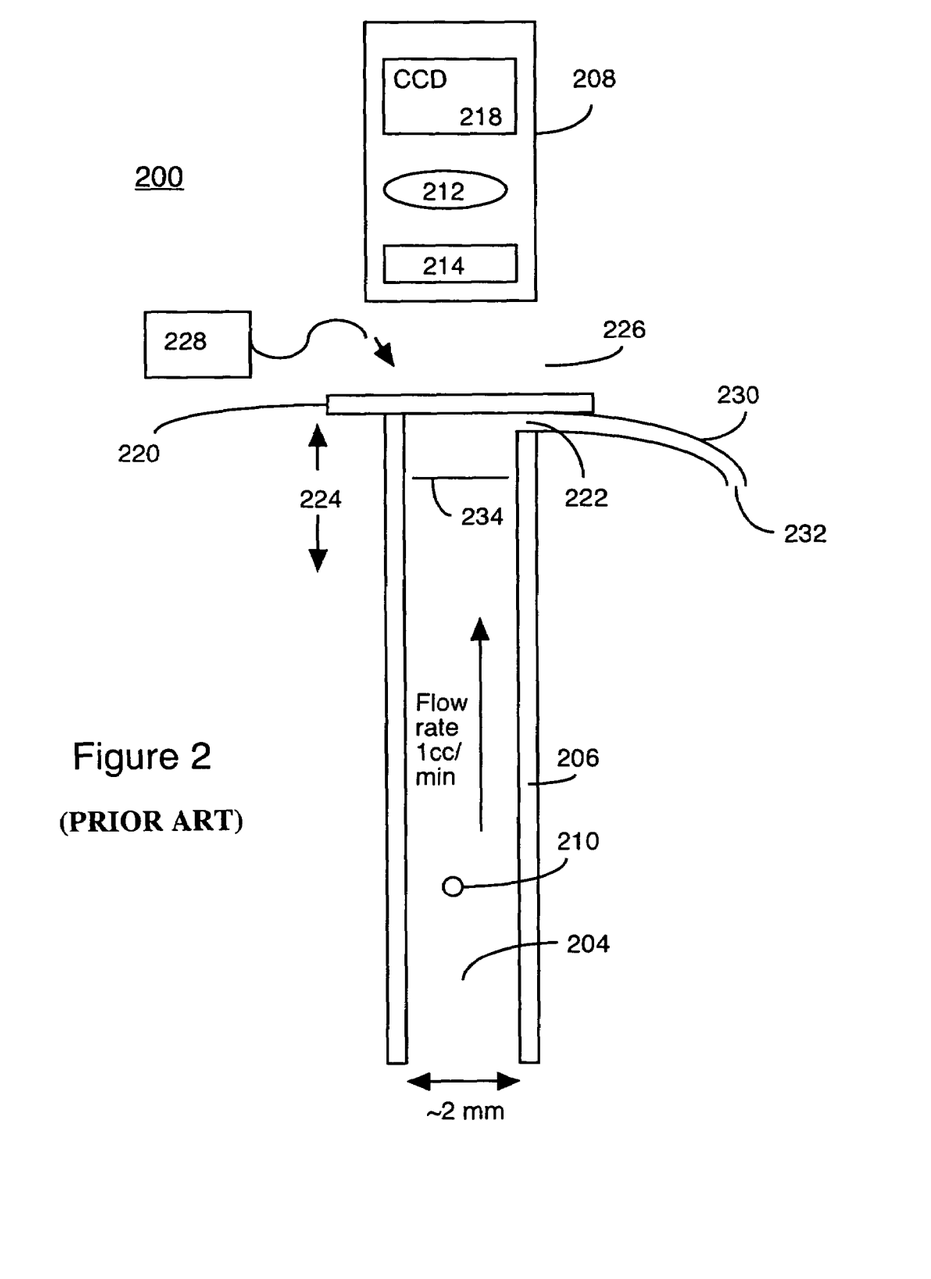
FIG. 2 (Prior Art) is a simplified schematic drawing showing apparatus for detecting particles in a translucent flow according to a precursor of the present invention.

A precursor invention, described in U.S. patent application Ser. No. 10/323,535 by the present inventor, is shown in FIGS. 2 and 3. This invention incorporates detection, but not high resolution imaging.

In FIG. 2 (Prior Art), a sample of fluorescently tagged cells 210 flows up the tube 206 toward the CCD camera and foreoptics 208. The cells are illuminated in the focal plane by a laser 228 through transparent end element 220. When the cell(s) pass through the CCD camera focal plane 234 they are imaged by the CCD camera 218 and lens assembly 212, through a transparent window and a filter 214 that isolates the wavelength of fluorescent emission. The fluid in which the cells are suspended then passes by the window and out the drain tube 230.

In FIG. 3 (Prior Art), a flow block 322 is used with a device like that shown in FIG. 1. FIG. 3A is a side schematic drawing of the aluminum flow block. FIG. 3B is a top plan view of the flow black. FIG. 3C shows a detail of the device flow and imaging. The sample enters the flow block through Tygon tube 312 and stainless steel tube 310 and exits through stainless steel tube 324 and Tygon tube 315. Two 2-mm holes have been drilled into the aluminum flow block 322, an entrance hole 302 and an exit hole 306. As the sample flows up the internal entrance hole 302, it passes through the focal plane of the CCD camera 326. This hole is generally painted black to reduce scattered light. Component 320 is a Teflon tape gasket. The gasket is sandwiched between the aluminum flow block and a circular window 220, and tightly held with a screw-on brass cap 318. The gasket is cut to form a channel 304 through which the fluid is diverted into the exit hole 306. FIG. 3D is a photograph of a working flow block with attached tubing. The block is mounted onto a black-anodized plate.

A need remains in the art for improved apparatus and methods for high throughput, high resolution imaging analysis of samples in a translucent flowing liquid.

SUMMARY OF THE INVENTION

It is an object of the present invention to provide improved apparatus and methods for high throughput, high resolution imaging analysis of samples in a translucent flowing liquid. This object is accomplished by utilizing flow cytometry to first detect particles and then to reposition and magnify detected particles for high resolution imaging.

The present invention provides apparatus and methods for high throughput, high sensitivity imaging and classification of samples in a translucent or transparent flowing liquid. This object is accomplished by providing a relatively large cross section axial flow, in which cells or other target particles suspended in a liquid are observed as they are quickly passed through a tube oriented generally along the optical axis of imaging optics. When a rare cell of interest is detected, it is slowly passed back through the tube and imaged. This allows for real time high resolution imaging of rare cells, including multi-spectral imaging, without having to resort to labor-intensive microscopy or more complex and expensive MSIFC.

The present invention has advantages over Multi-Spectral Imaging Flow Cytometry (MSIFC), including detection of individual cells, at a much lower complexity, and thus cost. This invention is especially useful for real-time imaging of rare cells in a sample flow. This invention is based on taxonomic identification using fluorescent dyes.

Cells of interest are dyed with one or more fluorescent probes or markers designed to stain regions of the cell that are of particular interest. The cells are passed in a vertical stream of liquid toward a laser diode, LED, gas laser, or the like, or a combination of the above at one or more wavelengths which illuminate the fluorescent dyes and cause them to fluoresce at a longer wavelength than the wavelength of illumination.

In order to substantially increase the power of this invention, the following features are included in various preferred embodiments:

1) By using several computer selectable parfocal objective lenses the user can image the entire field of view and then zoom in on a particular cell at substantially higher resolution.

2) By mounting the flow cell on a computer controlled x-y stage, the user can center a portion of the image on which to zoom or increase magnification.

3) By using a computer-controlled syringe pump that is bidirectional (can pump forward or backward) along with a computer selectable set of parfocal objective lenses and a computer controlled x-y stage on which to mount the flow cell.

A low-cost CCD (charge coupled device) 2-D detector images the fluorescence emission each time a marked cell illuminated by the laser diode passes through the focal plane of the detector.

Background fluorescence from unbound dye or out-of-focus target particles/cells, can be removed by use of high-pass filtering of the images or by structured illumination techniques as outlined in Neil, Juskaitis, & Wilson (1997, Opt. Lett. 22, 1905–1907) and Fukano and Miyawaki (2003, Applied Optics 42, 19, 4119–4124).

Multi-spectral cell images are processed to retrieve morphology parameters such as overall size, nuclear size, nuclear shape, optical density, the detection and characterization of numerous fluorescent markers and FISH probes, the quantification of the total amount of DNA in the nucleus, and the detection of other cellular components such as fetal hemoglobin. Cells can then be classified according to these parameters or alternatively with automated classification algorithms such as Principal Component Analysis.

The present invention includes apparatus and methods for imaging particles in a sample of liquid flowing within a flow channel along a flow axis including a transparent element transverse to the flow axis for terminating the flow channel and diverting the sample, a waste conduit adjacent to the transparent element for discharging the sample, an illumination beam(s) positioned to illuminate an illumination zone within the sample, and an imaging element(s) for imaging a focal plane transverse to the flow axis within the illumination zone.

Generally the focal plane is spaced apart from the transparent element and a clear volume separates the transparent element and the imaging element.

The imaging element comprises a color filter, optics, and a CCD camera.

The waste conduit may comprise an opening formed in the flow channel, or a specially designed flow block. The flow block includes an input tube for providing the sample to the flow block, an output tube for discharging the sample from the flow block, and a flow path formed within the flow block and connected to the input tube and the output tube. The flow path passes adjacent to the transparent element, and the focal plane is located in the flow path before the sample passes adjacent to the transparent element.

The illumination may be provided by a laser or by an LED, combined with the use of dichroic mirrors to allow multiple wavelength simultaneous illumination.

In the case of detection of pathogenic microorganisms in human blood, the resulting sample would contain red blood cells, and would likely be optically thick over circa 1 mm or greater distance necessitating a transparent gap (air or immersion liquid) between imaging optics and the focal plane of the instrument.

BRIEF DESCRIPTION OF THE DRAWINGS

FIG. 4B is a simplified view of a filter wheel of FIG. 4A, end on.

FIGS. 5A–5D are schematic drawings illustrating two images of the same cell at different wavelengths.

DETAILED DESCRIPTION OF THE PREFERRED EMBODIMENTS

The present invention includes apparatus and methods for high resolution imaging of fluorescent particles in a fountain flow cytometry set up. (A precursor invention, described in U.S. patent application Ser. No. 10/323,535 by the present inventor, is shown in Prior Art FIGS. 2 and 3. This previous invention incorporates detection, but not high resolution imaging.) To review the flow cytometry detection process, a flow channel defines a flow direction for samples in a flow stream and has a viewing plane nearly perpendicular to the flow direction. A clear volume between the illuminated flow volume and the imaging optics is provided in some embodiments. A beam of illumination is formed as a column having a size that can effectively cover the viewing plane, and illuminates the flow end on or nearly end on. Imaging optics are arranged to view the focal plane to form a low-resolution image of the multiple fluorescent sample particles in the flow stream. In this step, particles of interest are identified.

In th identification step, as a microorganism passes up the delivery tube its spot size (the size that the image of the microorganism occupies on the CCD) decreases as it approaches the focal plane of the CCD camera; above the focal plane the spot size increases. The spot size reaches it minimum in the focal plane of the CCD fore-optics. In order to minimize the blur of imaged cells, low resolution detection imaging should occur in a thin (relative to the camera focal length) focal plane and light emitted from outside of this region should be attenuated. This can be achieved by illumination of the flow with an elongated laser beam orthogonal to the flow (as in U.S. Pat. No. 6,309,886 by Ambrose et al.), or the use of structured illumination with a grating in the conjugate focal plane (Neil, Juskaitis, & Wilson, 1997, Opt. Lett. 22, 1905–1907) or using a micro-mirror array (Fukano and Miyawaki, 2003, Applied Optics 42, 19, 4119–4124).

Once a particle of interest has been detected, the present invention provides apparatus and methods for repositioning the particle, magnifying it, and forming a high resolution image of the image. For the present application, "low resolution" generally refers to an image on the order of 10–100 pixels. Such an image identifies that a spatially unresolved cell or particle is present. "High resolution" indicates a spatially resolved image of a particle, having 500 to 1000 or more pixels.

The low resolution imaging can be done on the fly with the high throughput apparatus shown in FIG. 2 (Prior Art). The ability to stop temporarily and form high resolution images of particles of interest, and then continue with the high throughput operation, is the key to the present invention.

Figure 3A:
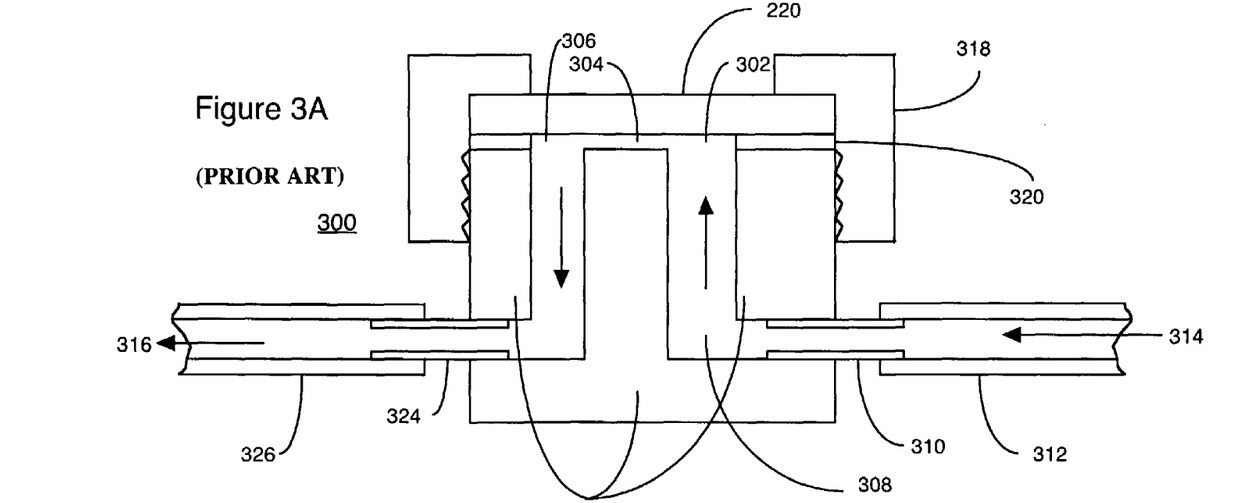
FIG. 3A (Prior Art) shows a side cutaway view of a flow block which may be used in the apparatus of FIG. 2.
Figure 3B:
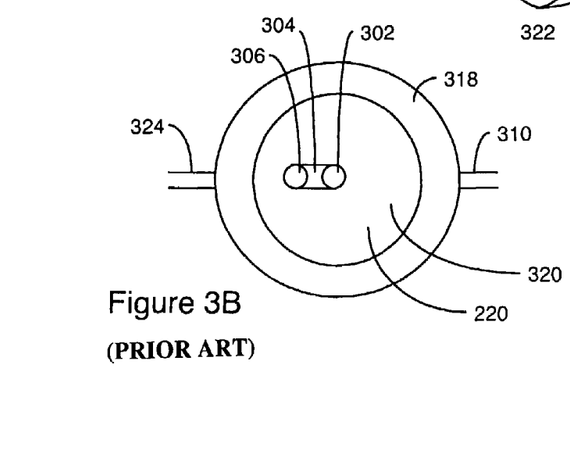
FIG. 3B (Prior Art) is a top plan view of the flow block.
Figure 3C:
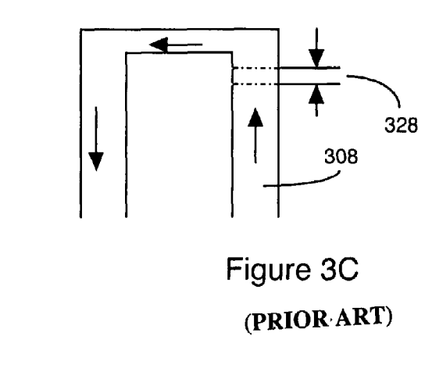
FIG. 3C is a detail side view of the flow block illustrating depth of focus.
Figure 3D:
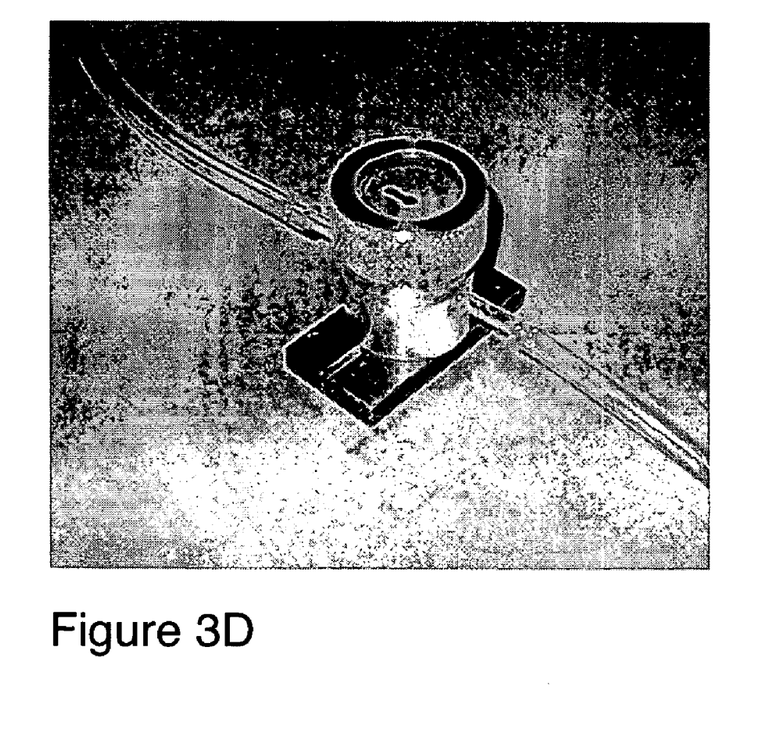
FIG. 3D is photograph of the flow block of FIG. 3A.
Figure 4A:
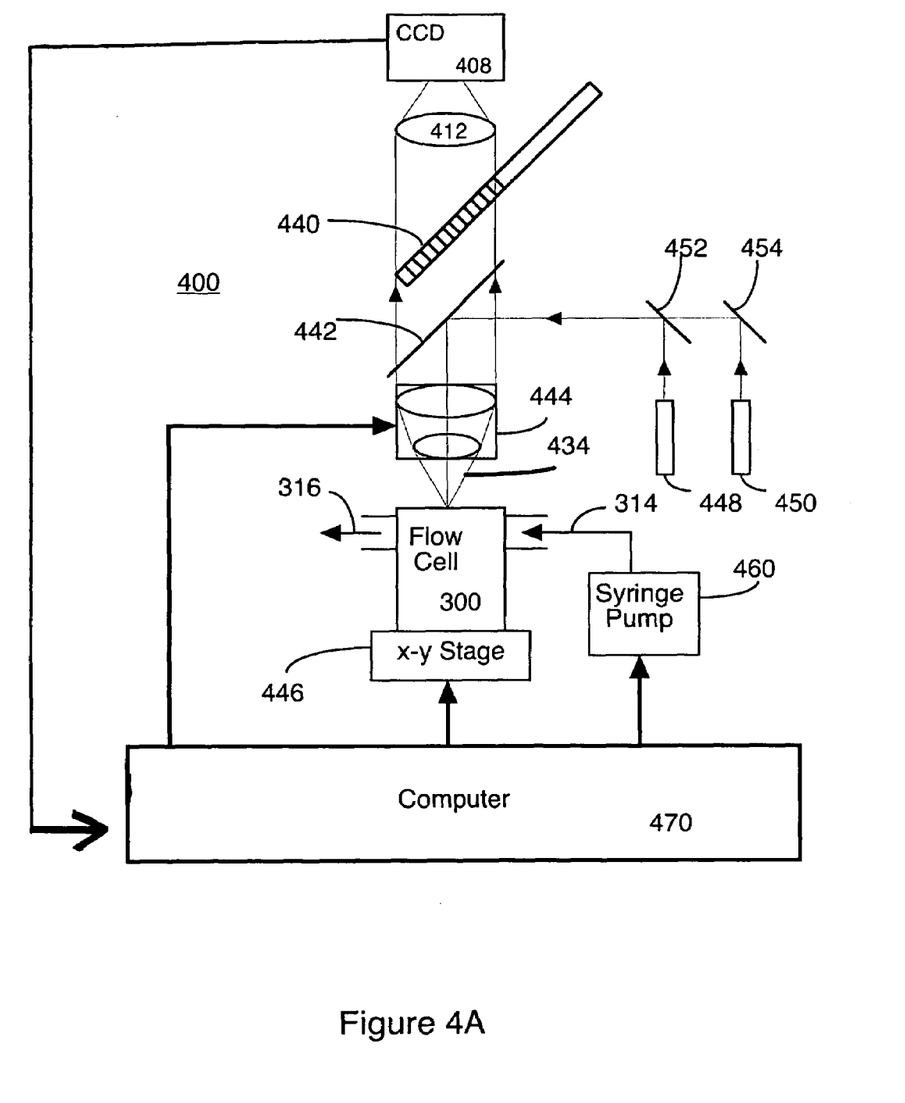
FIG. 4A is a block diagram illustrating a first embodiment of a high resolution imaging fountain flow cytometer according to the present invention.

A preferred embodiment of the present invention is shown in FIG. 4A. Refer also to Prior Art FIGS. 2 and 3A–3D. FIG. 2 illustrates illumination and detection of a target particle 210, and FIGS. 3A–3D illustrate a flow block which is useful in the present invention. FIG. 4A is a block diagram illustrating a high resolution imaging fountain flow cytometer 400 according to the present invention. The sample 314 is illuminated in this embodiment by multiple lasers 448, 450 through the microscope objective 444.

Multispectral imaging may be accomplished by using two separate lasers 448, 450 to illuminate sample 314 at different light frequencies, as shown in FIG. 4A. As an alternative, an illumination beam at a single frequency could result two different wavelengths of light being emitted from the particle in the sample, for example by illuminating two fluorescent dyes that emit at two different frequencies. In either case, two (or more) frequencies of light end up issuing from the particle (via reflection, emission, scattering, or the like) and are imaged, resulting in a multi-spectral image.

The flow cell 300 sits on a computer controlled x-y stage 446 that allows the field of view to be centered on any target particle 210 passing through the flow cell orifice. The microscope objective 444 can be swapped by computer control to allow for multiple magnifications (say 2×, 40×, and 100×). A filter wheel 440 allows imaging at multiple wavelengths. The syringe pump 460 is under computer control and may be programmatically stopped and run in either direction.

In this preferred configuration, the illumination geometry is an epi-illumination geometry, that is sample 314 is illuminated through the same microscope objective 444 that is used to image the sample, as is common with epi-fluorescent microscopes.

Whenever a cell of interest, 210, is detected passing through flow cell 300 by means of its fluorescence at a specific wavelength, the syringe pump 460 is used to slowly back cell 210 through the focal plane 326 of flow cell 300 by operating it in reverse at slow speed. As an alternative, or in addition, syringe pump 460 may be operated to stop the cell in the focal plane temporarily. Then x-y stage 446 is used to center cell 210 in the field of view while a high magnification objective lens 444 is selected and used to zoom in on the cell at higher magnification. Then a series of high resolution fluorescence images (see FIG. 5) at a series of absorption/emission wavelengths is taken for multispectral analysis by (for example) use of a computer controlled filter wheel 440. When completed, computer 470 resets filter 440, x-y stage 446, and microscope objective 444 so that syringe pump 460 can be set in forward motion at high speed again. All of this allows high speed detection of rare cells at high volume throughput, with high resolution imaging of cells of interest after detection from emission at a single wavelength (by using an appropriate selective stain, such as an immuno-label).

Figure 4B:
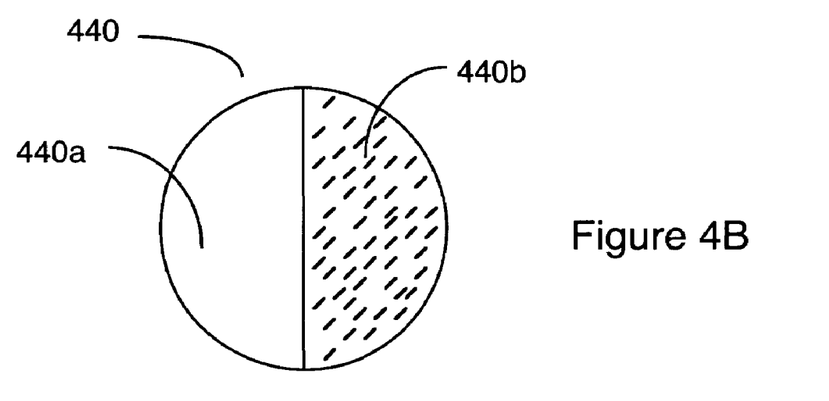
Figure 4C:
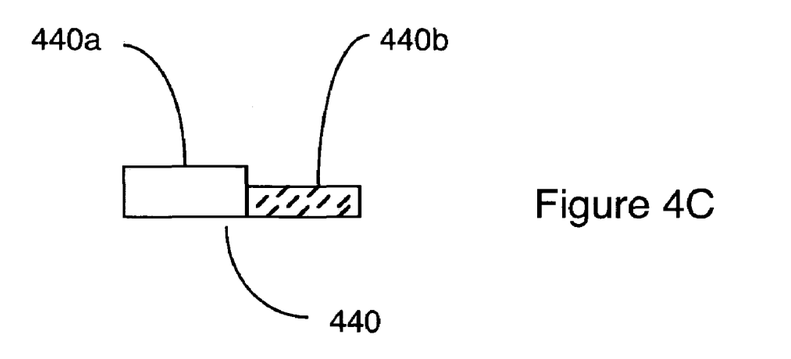
FIG. 4C is a simplified view of a filter wheel of FIG. 4A, from the side.

FIG. 4B is a simplified view of filter wheel 440 of FIG. 4A, shown end on. FIG. 4C is a simplified view of filter wheel 440, from the side. Filter wheel 440 and its operation are described in more detailed in U.S. patent Ser. No. 10/323,535. A summary of that discussion follows. Two-color emission is illustrated in FIGS. 4A–4C, but three or more colors may be detected by using more than two filter portions 440a, 440b, etc. While filter wheel 440 is not necessary for the present invention, since the two images can be taken at separate times, it is still useful in some embodiments for spatially separating the two (or more) resulting images.

The basic premise for the filter wheel system is that multicolor light emission 434 from focal plane 326 of flow cell 300 is sent through tilted filter wheel 440, which is rotating. As filter wheel 440 rotates it alternates between passing emission from a first emission wavelength and a second emission wavelength through the system onto CCD 408.

When a beam of light passes through tilted filter portions 440a, 440b, the beam is displaced by an amount that depends on the index of refraction and the thickness of each filter portion. Filter portions 440a, 440b, are designed to have slightly different thicknesses/indices, creating a multiple image for each bacterium or other imaged particle, one image for each emission color.

Filter wheel 440 rotates very rapidly compared to the integration (exposure) time, so that beam 434 is incident on each filter portion for (typically) half of the integration time. The two slightly displaced, colored beams then focus onto CCD 408, forming spots 502 and 504 in FIG. 5. The filter segment sizes can be adjusted to compensate for the difference in intensity at each wavelength.

Multicolor detection of three or more colors can easily be implemented with the invention. A motorized filter wheel 440 containing multiple filter segments (one to select each wavelength of multiple emission wavelengths) is inserted so that each segment will pass through beam 434 before striking the CCD 408 (or other imaging detector). The filter motor (not shown) is driven at a high rotation rate so that the time of rotation is much faster than the time it takes a particle to move in the image or across the focal plane. The filters are of differing index of refraction and/or thickness, so that the image of a particle on the detector will move (chop) significantly and in a direction and distance on the detector that can be calibrated. The detection of multiple spots on the detector with an appropriate distance and direction of separation can then be taken as a detection in one or more wavelength bands.

Figure 5A:
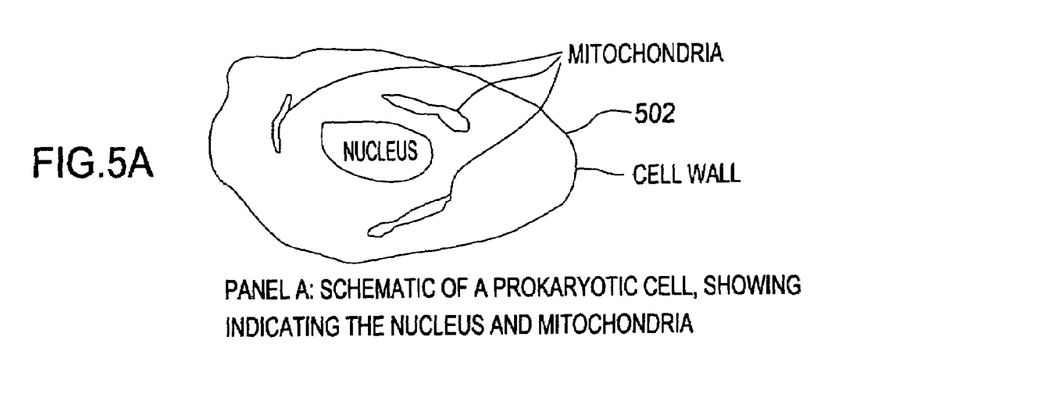
FIG. 5A shows the cell itself.
Figure 5B:
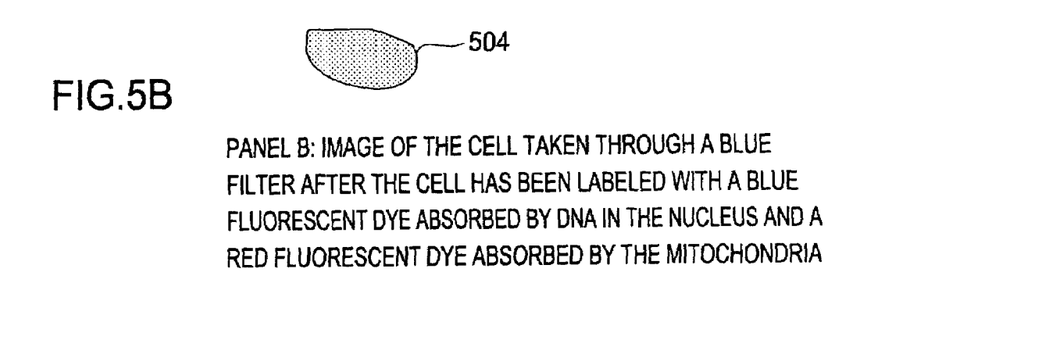
FIG. 5B shows an image of the cell of FIG. 5A at a first wavelength.
Figure 5C:
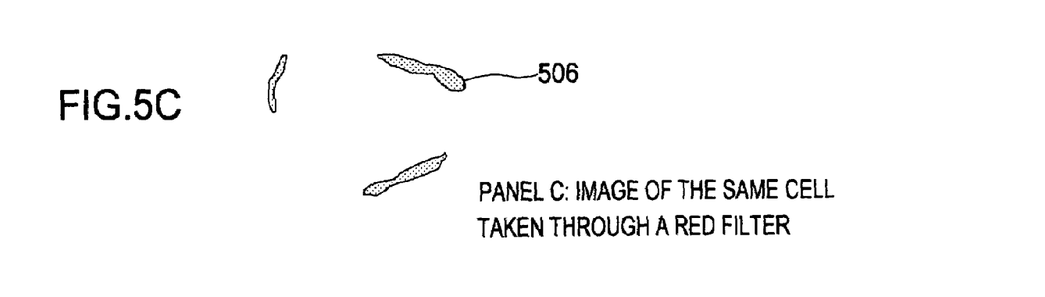
FIG. 5C shows an image of the cell of FIG. 5A at a second wavelength.
Figure 5D:
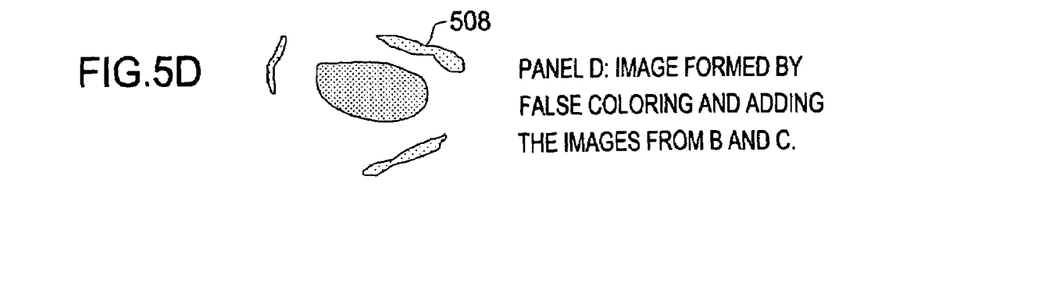
FIG. 5D shows a composite figure combining the images at both wavelengths.

FIGS. 5A–5D are schematic drawings illustrating two images of the same cell 502 at different wavelengths. FIG. 5A shows the cell 502 itself. FIG. 5B shows an image 504 of the cell of FIG. 5A at a first wavelength, and FIG. 5C shows an image of the cell of FIG. 5A at a second wavelength. For example, if cell 502 was labelled with a blue fluorescent dye absorbed by the DNA of the nucleus, and a red fluorescent dye absorbed by the mitochondria, image 504 could be the image resulting applying a blue filter, and image 506 could be the image resulting from applying a red filter. Essentially, images 504, 506 are cartoons showing two MSFFC images of a cell, side-by-side, at two emission wavelengths. Each shows a different morphology, which can be used for cell identification/discrimination. FIG. 5D shows a composite figure 508 combining the images at both wavelengths. For example, image 508 could be an image formed by false coloring and adding images 504 and 506.

Figure 6A:
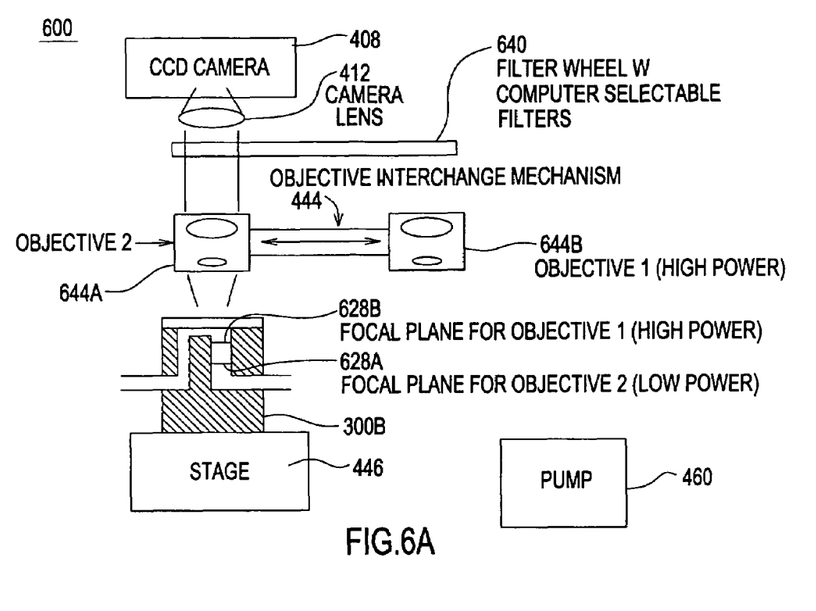
FIG. 6A is a block diagram illustrating a second embodiment of a high resolution imaging fountain flow cytometer according to the present invention with two focal planes and a variation on the filter wheel element.

FIG. 6A is a block diagram illustrating a second embodiment 600 of a high resolution imaging fountain flow cytometer according to the present invention with two focal planes 628A and 628B and possible variations 640 on the filter wheel element. In the embodiment of FIG. 6, microscope objective 444 comprises a low power objective 644A and a high power objective 644B. Low power objective 644A has a first focal plane 628A, and High power objective 644B has a second focal plane 628B, which is downstream of focal plane 644A.

In use, low power objective 644A is used most of the time, while imaging cytometer 600 is doing high-speed detection of target particles. When a target particle 210 is detected, microscope objective 444 switches resolutions, for example by sliding low power objective 644A out of the optical axis and sliding high power objective 644B into the optical axis in its place. XY stage 446 operates to center particle 210 within high power objective 644B. Flow control element 460 sows the flow through flow cell 300B. Hence, by the time target particle 210 passes through second focal plane 628B, it can be imaged by high power objective 644B. Processor 670 detects target particle 210, and then changes objectives, centers the particle, and controls the flow for high resolution imaging.

Figure 6B:
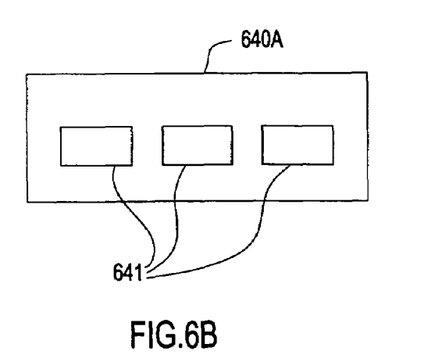
FIG. 6B is a simplified view of a filter slide element from the side.
Figure 6C:
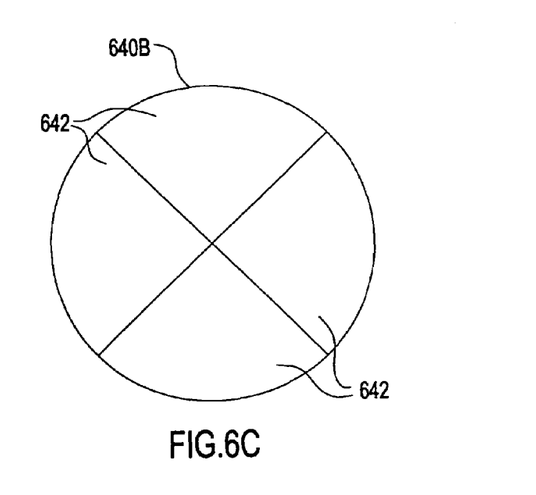
FIG. 6C is a simplified view of a flat filter wheel from the side.

FIG. 6B is a simplified view of a filter slide element 640A from the side. FIG. 6C is a simplified view of a flat filter wheel 640B from the side. These filter elements include filters 641, 642 at two or more wavelengths (colors) for multispectral imaging. Since the flow is slowed or stopped while high resolution imaging occurs, these flat filter elements may be used in place of the filter wheel 440 shown in FIG. 4. They do no spatially displace the images, but the images are displaced in time.

Figure 7:
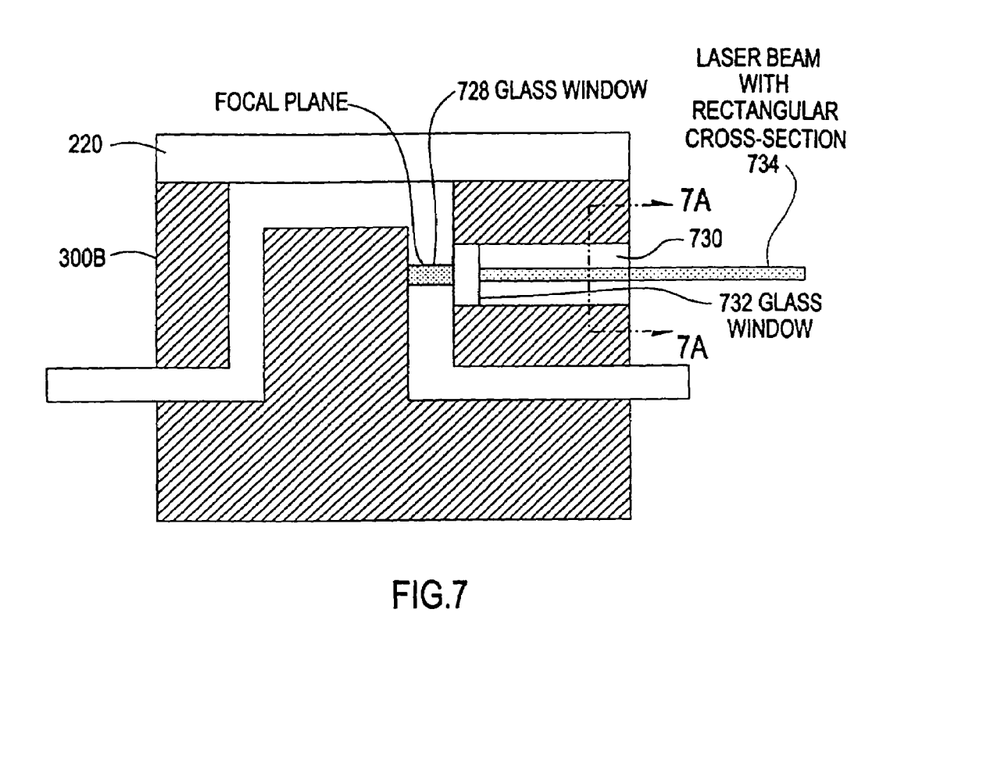
FIG. 7 shows a side cutaway view of a variation of the flow block of FIG. 3, utilizing side illumination.
Figure 7A:
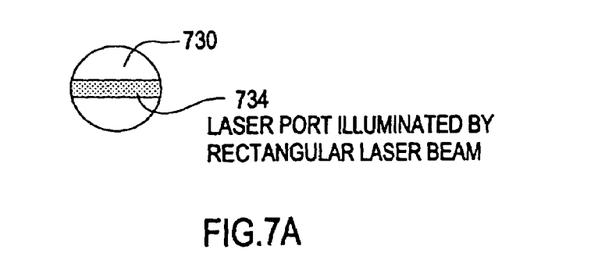
FIG. 7A shows an end-on view of the laser port of FIG. 7.

FIG. 7 shows a side cutaway view of a variation 300C of the flow block 300 of FIG. 3, utilizing side illumination. Imaging is still done through transparent element 220, but in some cases it is convenient to utilize side illumination. Port 730 allows laser beam 734 to illuminate focal plane 728 through window 732.

A number of alternative embodiments are within the scope of the present invention. For example, while the preferred embodiment of FIG. 4 includes multi-spectral imaging, one-color imaging is also quite useful. The flow cell of FIG. 3 is a particularly useful element of the invention, but can be replaced with a simpler element such as that shown in FIG. 2.

What is claimed is:

1. Apparatus for imaging particles in a sample of liquid flowing within a flow channel along a flow axis comprising:
   a transparent element transverse to the flow axis for terminating the flow channel and diverting the sample;
   a waste conduit adjacent to the transparent element for discharging the sample;
   an illumination beam positioned to illuminate an illumination zone within the sample;
   an imaging element adjacent to the transparent element for imaging a first focal plane transverse to the flow axis within the illumination zone and for generating a signal based upon the image;
   a processor connected to the imaging element for identifying a particle in the flow based upon the signal;

a flow control element for repositioning the identified particle by modifying the sample flow, responsive to the processor identifying a particle; and optics for generating a high resolution image of the repositioned particle.

2. The apparatus of claim 1, further comprising apparatus for generating a multi-spectral high resolution image wherein the illumination beam causes two different wavelengths of light to issue from the particle and further including means for separating the images resulting from each wavelength of issued light.

3. The apparatus of claim 2, wherein the means for separating comprises: a generally planar filter wheel located between the transparent element and the imaging element, the filter wheel plane tilted with respect to the optical axis of the imaging element, wherein the filter wheel includes at least two filter portions, each filter portion having a different thickness or index of refraction; a filter wheel motor for rotating the filter wheel such that illumination from the illumination zone passes through each filter portion and is imaged by the imaging element during part of the integration time; wherein spaced apart images of each imaged particle is formed for each filter portion.

4. The apparatus of claim 2, wherein the means for separating comprises a generally planar filter wheel located between the transparent element and the imaging element, the filter wheel plane generally transverse to the optical axis of the imaging element, wherein the filter wheel includes at least two filter portions, each filter portion transmitting different light wavelengths; and means for selectively intersecting the optical axis with a desired filter portion.

5. The apparatus of claim 2, wherein the means for separating comprises a generally planar filter slide located between the transparent element and the imaging element, the filter slide plane generally transverse to the optical axis of the imaging element, wherein the filter slide includes at least two adjacent filter portions, each filter portion transmitting different light wavelengths; and means for selectively intersecting the optical axis with a desired filter portion.

6. The apparatus of claim 1, wherein the waste conduit comprises a flow block including: an input tube for providing the sample to the flow block; an output tube for discharging the sample from the flow block; a flow path formed within the flow block and connected to the input tube and the output tube; wherein the flow path passes adjacent to the transparent element; and wherein the focal plane is located in the flow path before the sample passes adjacent to the transparent element.

7. The apparatus of claim 6 wherein the illumination beam passes through the transparent element.

8. The apparatus of claim 6, further comprising a window adjacent to the focal plane and wherein the illumination beam passes through the window.

9. The apparatus of claim 6, further comprising an x-y stage connected to the flow block and responsive to the processor for moving the flow block in order to center the particle relative to the optics.

10. The apparatus of claim 1 wherein the optics include selectable elements of varying power, including a lower magnification objective for imaging the focal plane and a higher magnification objective for generating the high resolution image.

11. The apparatus of claim 10 wherein the first focal plane is the focal plane of the lower magnification objective, wherein a second focal plane positioned downstream of the first focal plane is the focal plane of the higher magnification objective, and further comprising:

an xy stage responsive to the processor for centering the particle relative to the higher magnification objective after the particle traverses the first focal plane and before it traverses the second focal plan; and wherein the flow control element includes mean for slowing the flow after the particle traverses the first focal plane.

12. The apparatus of claim 10, further comprising a CCD camera for capturing the high resolution image.

13. The apparatus of claim 10, wherein the optics further comprise a sliding element housing the objectives adjacent to one another.

14. The apparatus of claim 1, wherein the illumination beam illuminates the illumination zone through the transparent element.

15. The apparatus of claim 14 wherein the illumination beam is positioned to travel through the optics.

16. The apparatus of claim 1 wherein the flow control element comprises a bi-directional pump.

17. A method for imaging particles in a sample of liquid flowing within a flow channel along a flow axis comprising the steps of:

a) terminating the flow channel and diverting the sample flow with a transparent element;
b) illuminating an illumination zone within the sample;
c) imaging a first focal plane transverse to the flow axis within the illumination zone;
e) generating a signal based upon the first focal plane image;
d) identifying a particle in the sample flow based upon the signal;
e) repositioning the identified particle by modifying the sample flow; and
f) generating a high resolution image of the repositioned particle.

18. The method of claim 17, wherein step (f) generates a multi-spectral image.

19. The method of claim 17, wherein step (e) repositions the particle at the first focal plane.

20. The method of claim 17, wherein step (e) repositions the particle at a second focal plane.

21. The method of claim 17, wherein the illumination beam illuminates the sample through the transparent element.

22. Apparatus for imaging particles in a sample of liquid flowing within a flow channel along a flow axis comprising the steps of:

transparent means for terminating the flow channel and diverting the sample flow;
means for illuminating an illumination zone within the sample;
means for imaging a first focal plane transverse to the flow axis within the illumination zone;
means for generating a signal based upon the first focal plane image;

means for identifying a particle in the sample flow based upon the signal;

means for repositioning the identified particle by modifying the sample flow; and means for generating a high resolution image of the repositioned particle.

23. The apparatus of claim 22, wherein the step of generating a high resolution image generates a multi-spectral image.

24. The apparatus of claim 22, wherein the means for repositioning repositions the particle at the first focal plane.

25. The apparatus of claim 22, wherein the means for repositioning repositions the particle at a second focal plane.

26. The apparatus of claim 22, wherein the illumination means illuminates the sample through the transparent means.

* * * * *